United States Patent
Arndt et al.

(10) Patent No.: US 8,388,613 B1
(45) Date of Patent: Mar. 5, 2013

(54) METHODS AND APPARATUS FOR MICROWAVE TISSUE WELDING FOR WOUND CLOSURE

(75) Inventors: G. Dickey Arndt, Friendswood, TX (US); Phong H. Ngo, Friendswood, TX (US); Chau T. Phan, Sugar Land, TX (US); Diane L. Byerly, Seabrook, TX (US); John R. Dusl, Houston, TX (US); Marguerite A. Sognier, Houston, TX (US); James R. Carl, Houston, TX (US)

(73) Assignee: The United States of America as represented by the Administrator of the National Aeronautics and Space Administration, Washington, DC (US)

(*) Notice: Subject to any disclaimer, the term of this patent is extended or adjusted under 35 U.S.C. 154(b) by 587 days.

(21) Appl. No.: 12/757,657

(22) Filed: Apr. 9, 2010

(51) Int. Cl.
    *A61B 18/14* (2006.01)
(52) U.S. Cl. .......... 606/33; 606/49; 606/41; 607/101
(58) Field of Classification Search .......... 606/27–34, 606/41, 48–50, 213; 607/101–102, 154, 607/156
    See application file for complete search history.

(56) References Cited

U.S. PATENT DOCUMENTS

| | | | | |
|---|---|---|---|---|
| 5,156,613 A | * | 10/1992 | Sawyer | 606/213 |
| 5,334,191 A | | 8/1994 | Poppas et al. | |
| 5,571,216 A | * | 11/1996 | Anderson | 128/898 |
| 5,669,934 A | | 9/1997 | Sawyer | |
| 5,749,895 A | * | 5/1998 | Sawyer et al. | 606/214 |
| 5,824,015 A | | 10/1998 | Sawyer | |
| 5,925,078 A | | 7/1999 | Anderson | |
| 6,033,401 A | * | 3/2000 | Edwards et al. | 606/41 |
| 6,211,335 B1 | | 4/2001 | Owen et al. | |
| 6,323,037 B1 | | 11/2001 | Lauto et al. | |
| 6,583,117 B2 | | 6/2003 | Owen et al. | |
| 6,607,522 B1 | | 8/2003 | Hamblin et al. | |
| 7,033,348 B2 | | 4/2006 | Alfano et al. | |
| 7,077,839 B2 | | 7/2006 | Hamblin et al. | |
| 7,128,739 B2 | | 10/2006 | Prakash et al. | |
| 7,211,080 B2 | | 5/2007 | Treat et al. | |
| 7,588,565 B2 | * | 9/2009 | Marchitto et al. | 606/27 |
| 2002/0045732 A1 | | 4/2002 | Owen et al. | |
| 2003/0191496 A1 | | 10/2003 | Edwards et al. | |
| 2003/0216718 A1 | | 11/2003 | Hamblin et al. | |
| 2003/0216729 A1 | * | 11/2003 | Marchitto et al. | 606/41 |
| 2004/0073256 A1 | | 4/2004 | Marchitto et al. | |
| 2004/0127895 A1 | | 7/2004 | Flock et al. | |
| 2005/0079997 A1 | | 4/2005 | Owen et al. | |
| 2007/0179484 A1 | | 8/2007 | Sade | |

FOREIGN PATENT DOCUMENTS

WO   WO 9104073   4/1991

* cited by examiner

*Primary Examiner* — Michael Peffley
(74) *Attorney, Agent, or Firm* — Theodore U. Ro

(57) ABSTRACT

Methods and apparatus for joining biological tissue together are provided. In at least one specific embodiment, a method for joining biological tissue together can include applying a biological solder on a wound. A barrier layer can be disposed on the biological solder. An antenna can be located in proximate spatial relationship to the barrier layer. An impedance of the antenna can be matched to an impedance of the wound. Microwaves from a signal generator can be transmitted through the antenna to weld two or more biological tissue pieces of the wound together. A power of the microwaves can be adjusted by a control circuit disposed between the antenna and the signal generator. The heating profile within the tissue may be adjusted and controlled by the placement of metallic microspheres in or around the wound.

20 Claims, 2 Drawing Sheets

METHODS AND APPARATUS FOR MICROWAVE TISSUE WELDING FOR WOUND CLOSURE

ORIGIN OF THE INVENTION

The invention described herein was made in part by employees of the United States Government and in part was made in the performance of work under a NASA contract subject to the provisions of Section 305 of the National Aeronautics and Space Act of 1958, Public Law 85-568 (72 Stat. 435; 42 U.S.C. 2457). The invention may be manufactured and used by and for the Government of the United States for governmental purposes without the payment of any royalties thereon or therefore.

BACKGROUND OF THE INVENTION

1. Field of the Invention

Embodiments of the present invention generally relate to methods and apparatus for biological tissue soldering. More particularly, embodiments of the present invention relate to methods and apparatus for microwave biological tissue soldering.

2. Description of the Related Art

Medical procedures and emergency response often necessitate joining two separate biological tissue pieces in order to promote wound healing or fusion of the biological tissue pieces. In addition, many procedures require the connection of prosthesis to a biological tissue within the body. These procedures can be done with conventional suturing, stapling, or with newer methods of suture-less biological tissue repair. However, conventional suturing and stapling techniques are time-consuming, and sutures and staples introduce foreign materials into the biological tissue, increasing the risk of infection or adverse immunological reaction. Suturing also disrupts the normal growth and cellular organization of the biological tissue and increases the risk of scar biological tissue formation, which can interfere with the function of the native biological tissue. Additionally, scar biological tissue may create undesired irregularities in the skin. Sutures can create an incomplete seal which leave gaps that can leak and cause complications.

In addition, newer methods of suture-less biological tissue repair are usually performed with lasers, which are difficult to use and often provide limited repeatable results. Welding biological tissue using a laser is a suture-less biological tissue repair method currently in development. However, laser welding systems typically require a cooling system. The cooling system is often complex and bulky. The bulky cooling system inhibits the ability to use conventional laser welding systems at emergency scenes. In addition, laser welding systems are difficult to use and require extensive training. As such, laser tissue welding devices are prone to error and require precise solders of uniform depth to achieve a seal and prevent tissue damage.

A need exists, therefore, for improved systems and methods for tissue welding that is transportable, reliable, and provides repeatable results.

SUMMARY OF THE INVENTION

Methods and apparatus for joining biological tissue together are provided. In at least one specific embodiment, a method for joining biological tissue together can include applying a biological solder on a wound. A barrier layer can be disposed on the biological solder. An antenna can be located in proximate spatial relationship to the barrier layer. An impedance of the antenna can be matched to an impedance of the wound. Microwaves from a signal generator can be transmitted through the antenna to weld two or more biological tissue pieces of the wound together. The power of the microwaves can be adjusted by a control circuit disposed between the antenna and the signal generator.

In at least one specific embodiment, a method for joining biological tissue together can include applying a biological solder to a wound. A barrier layer can be disposed on the biological solder. An antenna can be located in proximate spatial relationship to the barrier layer. An impedance of the antenna can be matched to an impedance of the wound. Microwaves from a signal generator can be transmitted through the antenna to weld two or more biological tissue pieces of the wound together. The power of the microwaves can be adjusted by a control circuit disposed between the antenna and the signal generator. A waveguide coupler connected between the power amplifier and the antenna can measure the forward (radiated) power and the reflected power from the antenna. This is a means to ensure the antenna and tissue are properly impedance matched.

In at least one specific embodiment, a method for joining biological tissue together can include applying a biological solder to a wound. A barrier layer can be disposed on the biological solder. An antenna can be located in proximate spatial relationship to the barrier layer. An impedance of the antenna can be matched with an impedance of the wound. Microwaves can be transmitted from a signal generator through the antenna to weld two or more biological tissue pieces of the wound together. The power of the microwaves can be adjusted by a control circuit disposed between the antenna and the signal generator. An output power from the antenna can be measured using a power monitor in communication with the antenna. A power reflected back to the antenna can be measured using a reflected power monitor in communication with the antenna. The impedance of the antenna should be adjusted to better match the tissue impedance when the ratio between the output power and the reflected power is less than or equal to about 5 decibels.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this patent is combined with available information and technology.

Figure 1:
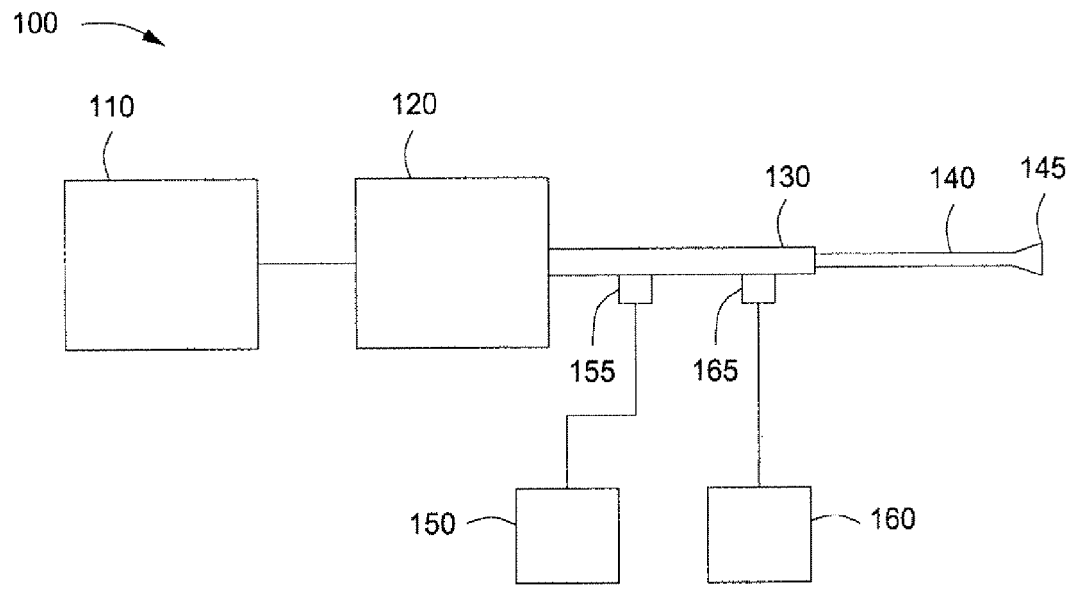
FIG. 1 depicts a schematic view of an illustrative microwave welding system, according to one or more embodiments described.

FIG. 1 depicts a schematic view of an illustrative microwave welding system 100, according to one or more embodiments. The microwave welding system 100 can be used to connect or weld two or more separate biological tissue pieces of a wound or incision together. Accordingly, the microwave welding system 100 can be used to close wounds or incisions. The microwave welding system 100 can also reduce infections or the likelihood of an infection occurring in or about a wound. The microwave welding system can also restore welded biological tissue to an original tensile strength. The wounds can be surface wounds, deep wounds, wounds to an organ, or other damage to biological tissue. For example, the microwave welding system 100 can be used to connect or weld two or more pieces of skin together.

The microwave welding system 100 can include a microwave signal generator or ("microwave generator") 110 in communication with an antenna 145, which may comprise a plurality of antennae. The microwave generator can also include a control circuit ("variable power amplifier") 120, a waveguide coupler 130, and a waveguide 140. An output power of the microwave welding system 100 can be varied by the variable power amplifier 120, which can be disposed between the antenna 145 and the microwave generator 110. As shown, the antenna 145 can be connected to the variable power amplifier 120 via the waveguide coupler 130 and the waveguide 140. The microwave welding system 100 can also include an output or forward power monitor 150 and a reflected power monitor 160 in communication with the antenna 145 and the microwave generator 110.

The microwave generator 110 can include a low-power signal source that can drive a power amplifier to provide a high power output signal. The microwave generator 110 can produce or generate desired microwave frequencies in the range of about 2 Gigahertz ("GHz") to about 40 GHz. For example, the microwave generator 110 can produce S-band, C-band, and Ka-band frequencies. Different frequencies can be used to treat different types of wounds. For example, a shallow wound can be treated with shorter wavelength Ka-band frequencies while a deeper wound may require longer wavelengths, such as S-band and/or C-band frequencies. Furthermore, Ka-band frequencies can cleanse a wound, e.g. kill at least a portion of any bacteria present in or about the wound, which can reduce the potential for infections to occur in or about the wound.

The microwave signal generator 110 can be or include a single frequency source, such as a Gunn oscillator or some other frequency source that can drive the variable power amplifier 120. The variable power amplifier 120 can include circuitry to control and change an input drive amplitude signal to the variable power amplifier 120. Feedback control can obtain information, e.g. automatically, from the forward power monitor 150 and the reflected power monitor 160. The output radiated power levels can be changed or altered while maintaining a given operating frequency.

The waveguide 140 can provide power to the antenna 145 from the variable power amplifier 120. The waveguide 140 can be or include a coaxial cable or a flexible waveguide. For example, the waveguide 140 for S-band and/or C-band can be a coaxial cable and the waveguide 140 for Ka-band can be a flexible waveguide. An illustrative waveguide 140 is discussed and described in U.S. Pat. No. 7,132,909, which is incorporated by reference herein. One or more dielectric materials can be disposed within (1) the waveguide 140 adjacent the antenna 145; and/or (2) the antenna 145. The dielectric material can control the impedance at an input into the antenna 145. As such, the proper selection of the dielectric material can ensure there is a predetermined proper impedance match with the antenna 145.

The waveguide 140 can be connected or joined to the variable power amplifier 120 and/or the antenna 145 by the waveguide coupler 130. The waveguide coupler 130 can be used to sample or monitor the output signal ("forward power") to the antenna 145. The waveguide coupler 130 can also be used to sample or monitor the power reflected by the antenna 145 ("reflected power"). Monitoring the forward power and/or the reflected power can ensure there is a predetermined or predefined acceptable impedance match between an aperture of the antenna 145 and an impedance exhibited by the a wound or tissue to be welded. Monitoring the forward power and/or reflected power can also detect changes in the forward power and/or reflected power than can indicate when a welding process is complete. For example, as a protein solder binds tissue together by welding, the reflected power can change, which can indicate the welding process is complete. However, the waveguide coupler is an optional component as monitoring the forward power and/or the reflected power is optional.

The impedance of the antenna 145 can be adapted to match the impedance of the wound and tissue surrounding the wound by adjusting an electrical impedance of the antenna 145. The electrical impedance through the antenna 145 can be adjusted by changing the dielectric material inside the antenna 145, changing the cross-sectional area of the antenna aperture 145, and/or changing the spatial distribution of the dielectric material. The antenna 145 can direct microwaves to a wound. The antenna 145 can be connected to the end of the waveguide 140. For example, the antenna 145 can be a horn antenna connected to the waveguide 140 or a reduced aperture formed into the waveguide 140. A different size or type of antenna 145 can be used for different types of wounds. For example, a long antenna 145 can be used to weld two separate biological tissue pieces of an internal wound together and a short antenna 145 can be used to weld two separate biological tissue pieces of a surface wound together. One reason to change the output impedance of the antenna 145 can be to match the impedance of the antenna 145 to the impedance of a wound and tissue surrounding the wound. When the impedances of the antenna 145 and the wound/surrounding tissue match, the power transferred from the antenna 145 into the wound/surrounding tissue can be maximized.

The power output from the variable power amplifier 120 can be changed or adjusted, which can depend, at least in part, on the depth and size of a wound to be welded. The variable power amplifier 120 can include one or more amplifiers, one or more variable attenuators, and other power output enhancing equipment. The variable power amplifier 120 can magnify or adjust the microwave output power by adjusting the amplitude of the output power from the power amplifier 120. The variable power amplifier 120 can be an analog or a digital circuit. The variable power amplifier 120 can be in communication with one or more control systems (not shown) that can adjust the power output based on measured data of the forward power monitor 150 and/or the reflected power monitor 160.

The forward power monitor 150 can be connected or coupled to the waveguide 140 by the waveguide coupler 130. The waveguide coupler 130 can be a directional coupler. The forward power monitor 150 can be a digital or analog power meter. The forward power monitor 150 can include one or more first sensors or heads 155. An individual first sensor 155 can be or include a thermocouple sensor, a torque vane sensor, a thermistor based power sensor, a diode based sensor, a microwave calorimeter, a bolometer, a quasi-optic pulsed microwave sensor, an electron-beam based sensor, or a Hall effect based sensor. Multiple first sensor 155 combinations can be used. The forward power monitor 150 can display the output power of the antenna 145 in decibels relative to 1 milliwatt ("dBm") or decibels relative to 1 watt ("dBW").

The reflected power monitor 160 can be connected or coupled to the waveguide 140 by the waveguide coupler 130 and configured to measure or monitor the power reflected back to the antenna 145. The reflected power monitor 160 can be any digital or analog RF power meter. The reflected power monitor 160 can have one or more second sensors or heads 165. An individual second sensor 165 can be or include a thermocouple sensor, a torque vane sensor, a thermistor based power sensor, a diode based sensor, a microwave calorimeter, a bolometer, quasi-optic pulsed microwave sensor, an electron-beam based sensor, or a Hall effect based sensor. Multiple second sensor 165 combinations can be used. The reflected power monitor 160 can display the power reflected back to the antenna 145 in dBm or dBW.

Figure 2:
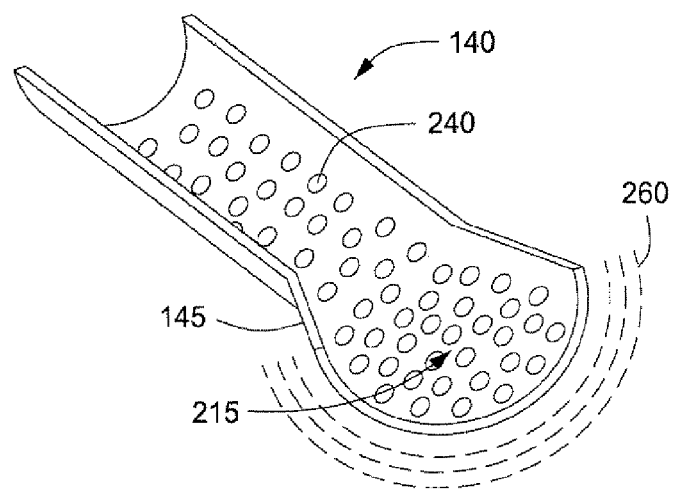
FIG. 2 depicts a cross-sectional view of an illustrative antenna connected to a waveguide, according to one or more embodiments described.

FIG. 2 depicts a cross-sectional view of an illustrative antenna 145 connected to a waveguide 140, according to one or more embodiments. The waveguide 140 and/or the antenna 145 can include a dielectric material 240 disposed therein. An aperture 215 can be formed into an end of the antenna 145. The antenna 145 can emit microwaves 260 through the aperture 215.

The waveguide 140 can be made from any suitable material. Illustrative materials can include, but are not limited to, gold, silver, copper, aluminum, stainless steel, other metals, or alloys thereof. The waveguide 140 can have a variety of cross-sectional shapes. For example, the cross-sectional shape of the waveguide 140 can be rectangular, circular, or elliptical. The cross-sectional area and shape of the waveguide 140 can be changed or adjusted to adjust or modify the impedance of the antenna 145. The waveguide 140 can be used to direct or control the direction of the microwaves 260 emitting therefrom. The microwaves 260 can emit from the aperture 215 formed into the antenna 145 and can be directed to a target location, such as a wound.

The dielectric material 240 can be or include solid dielectrics, such as powders, porcelain glass, fiberglass, and plastic. The dielectric material 240 disposed within the antenna 145 can match the antenna impedance to that of a wound and tissue surrounding a wound, which can in turn maximize the power transfer from the antenna 145 to the wound. The dielectric material 240 can also permit or allow the size and shape of the antenna 145 to change according to the characteristics of a particular wound. For example, the size of the aperture 215 formed into the antenna 145 can be reduced for lower frequencies, e.g. S-band and C-band, compared to the size of the aperture 215 when higher frequencies are used. Modifying the size, shape, number (i.e., a plurality of antennae), or any combination of the antenna 145 and/or the aperture 215 formed therein can provide a microwave welding system 100 (see FIG. 1) capable of radiating different types and sizes of wounds more effectively.

The aperture 215 formed into the antenna 145 can be formed from or in the waveguide 140, or, as shown, can be formed into the antenna 145. The aperture 215 can have any suitable cross-sectional shape. For example, the cross-sectional shape of the aperture 215 can be rectangular, circular, or elliptical. The aperture 215 can have a cross-sectional area ranging from a low of about 1 cm, about 2 cm, or about 3 cm to a high of about 8 cm, about 10 cm, or about 12 cm. In one or more embodiments, the aperture 215 can have an adjustable cross sectional area. The particular size and shape of the aperture 215 can depend, at least in part, on the operating frequency, whether a dielectric material 240 is disposed within the antenna, and/or other factors. The microwaves 260 can emit from the aperture 215.

The impedance of the antenna 145 can be matched to the impedance of the wound by changing or controlling the shape and size of the antenna 145, the aperture 215, and/or the dielectric material and its configuration within the antenna 145. For example, varying the cross-sectional area of the aperture 215 can increase or decrease the impedance of the antenna 145. The impedance of the antenna 145 can also be matched to the impedance of the wound by changing or controlling the type and amount of dielectric material 240 disposed within the antenna 145 adjacent the aperture 215 and/or within the waveguide 140 adjacent to the antenna 145. The waveguide 140 and the antenna 145 can be used to direct the microwaves 260 toward a wound and the microwaves 260 can emit from the antenna 145 through the aperture 215.

Figure 3:
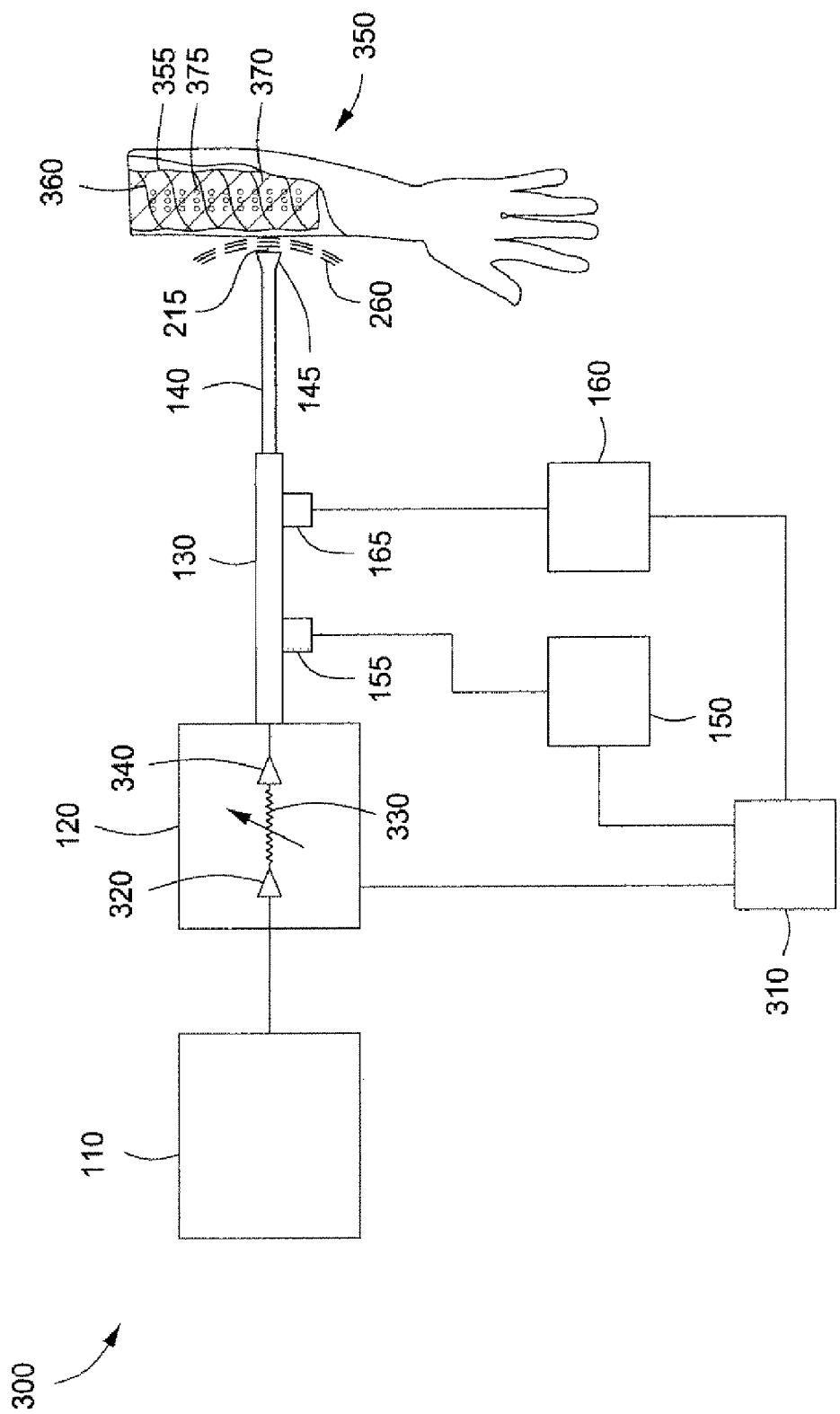
FIG. 3 depicts a schematic view of an illustrative microwave welding system joining two separate biological tissue pieces of a wound together, according to one or more embodiments described.

FIG. 3 depicts a schematic view of an illustrative microwave welding system joining two separate biological tissue pieces of a wound together, according to one or more embodiments. The microwave welding system 300 can be similar to the microwave welding system 100 discussed and described above with reference to FIGS. 1 and 2. The microwave welding system 300 can further include one or more processors 310 in communication with the forward power monitor 150, the reflected power monitor 160, and the variable power amplifier 120. The variable power amplifier 120 can include a preamp 320, a power amplifier 340, and a variable attenuator 330.

The wound 355 is shown on an arm 350, but it can be anywhere on the body. The wound can also be located on an animal of most any size, such as a rodent, dog, or horse. In addition, wounds located in or on body organs, such as the spleen or liver can be welded with the microwave welding system 300. A biological solder 370 can be applied to the wound 355 and a barrier layer 360 can be disposed about the biological solder 370. In one or more embodiments, microspheres 375 can be disposed in the wound 355. The microspheres 375 may be strategically or randomly disposed within the wound 355.

The preamplifier 320 can be a low gain, low power device that can help match the output of the microwave generator 110 to an input of the power amplifier 340. The preamplifier 320 can increase the power of the microwaves 260 leaving the antenna 145. The variable attenuator 330 can be a tee attenuator, a pi attenuator, a bridged tee attenuator, a reflection attenuator, or a balanced attenuator. The variable attenuator 330 can be adjusted to provide gain level adjustments to the microwave energy radiated by the power amplifier 340. The power amplifier 340 can have a fixed gain and can increase the amplitude of the microwaves leaving the variable attenuator 330 and passing therethrough by a set or predetermined amount. The power amplifier 340 can be a traveling wave tube (TWT) amplifier, a klystron amplifier, or any other solid state microwave amplifier.

The microspheres 375 can control the depth and location of heat penetration into the wound 355. As such, the microspheres 375 can provide or serve as a control mechanism to ensure that a desired temperature and heating profile is experienced by the wound 355 and surrounding tissue. The layer of microspheres 375 can act as a reflector to the microwave energy as it propagates through the biological tissue, in a manner similar to a metallic wire covering a glass door of a microwave oven. The biological tissue is heated by both absorption of the microwaves 260 by the biological tissue and thermal conduction through the biological tissue as a function of time in a region in front of the layer of the microspheres 375. Heating the biological tissue behind the layer of the microspheres 375 is only provided through thermal conduction. Accordingly, the layer of microspheres 375 can reduce and control the depth of the heating temperature profile.

The microspheres 375 can be premixed with the biological solder 370 or placed/disposed within the wound 355 prior to application of the biological solder 370 to the wound 355. For example, a layer of the microspheres 375 can be applied to the bottom of the wound 355 prior to the application of the biological solder 370 to the wound 355. The microspheres 375 can be or include a polymer encapsulating or containing metallic or other reflective particles. Reflective particles can be or include material that can reflect electromagnetic radiation. For example, reflective particles can reflect microwaves. It is not necessary to have a continuous sheet of microspheres 375 to reflect incident microwave energy. The separation between the microspheres 375 can be less than the wavelength of the radiated microwave energy. For example, the separation between microspheres when Ka-band energy is directed toward the wound can be less than about 0.5 cm.

The biological solder 370 can be disposed in, on, or otherwise about the wound 355 and heated by the microwaves 260 to solder or weld the biological tissue of the wound 355. The biological solder 370 can be or include one or more proteins. The proteins can be recombinantly or synthetically produced proteins, purified naturally occurring proteins, or a combination thereof.

In an embodiment, the biological solder 370 is comprised of a bovine serum albumin ("BSA") mixed with sterile water obtained from a Millipore Milli Q System. In another embodiment, the biological solder is comprised of any serum albumin, including that derived from humans. The biological solder 370 can include about 90 wt % to about 100 wt % of the BSA. For example, the biological solder 370 can include 90-100 grams of BSA per 100 milliliters ("ml") of sterile water. The biological solder 370 can be prepared by placing a predetermined amount, such as 90-100 grams, of the BSA in a sterile ml conical tube. A predetermined amount of the sterile water, such as 100 ml, can be added to the conical tube to form a water and BSA solution. The conical tube can be inverted intermittently, such as every 15 minutes, to mix the sterile water and BSA to provide a water and BSA mixture. In one or more embodiments, the mixture can be placed on a mechanical rocker. The mechanical rocker can rock the conical tube containing the BSA water mixture from about 20 times to about 40 times per minute until the BSA dissolves at room temperature to provide the biological solder 370. The solution can stand at room temperature for a period of time prior to applying the biological solder 370 to the wound 355. The biological solder 370 can be stored for approximately 2 months at room temperature without loss of efficacy in closing wounds.

The barrier layer 360 can be placed or disposed about the biological solder 370 to separate the antenna 145 from the biological solder 370. The barrier layer 360 can include gauze, a polyester film, a plastic sheet, or the like. The gauze may be comprised of biologically degradable material. For example, the barrier layer 360 can be a polymer film or sheet sold under the trademark MYLAR. The barrier layer 360 can provide a non-sticky interface between the antenna 145 and the biological solder 370. The barrier layer 360 can also provide a method for introducing biologically degradable gauze material into the solder, which can enhance the tensile strength of the biological solder 370.

An individual processor 310 can be a central processing unit ("CPU") or an electronic circuit capable of executing a predefined set of instructions. An individual processor 310 can have an electronic medium, such as a hard drive, that has computer instructions associated with performing certain functions. The functions can include, for example, calculating the ratio of the output power from the antenna 145 to the power reflected back to the antenna 145; shutting down the microwave welding system 300 if the measured output power from the antenna 145 and the power reflected back to the antenna 145 is outside a predetermined range; and/or adjusting the variable attenuator 330 to increase the output power of the antenna if the measured output power from the antenna 145 and the power reflected back to the antenna 145 is outside a predetermined range. The processor 310 can be in communication with the microwave generator 110, the forward power monitor 150, the reflected power monitor 160, the first and second sensors 155, 165, the variable power amplifier 120, or any combination thereof.

In operation, two or more biological tissue pieces of the wound 355 on the body part 350 can be welded or joined together using the welding system 300. The body part 355 can be any body part. For example, the wound 355 can be a surface wound, a deep-cut wound, skin tears, skin rips, and internal organs such as the liver, spleen, and kidneys that can be welded back together.

The wound 355 can be prepared for welding by introducing the microspheres 375 to the wound 355. The microspheres 375 can be introduced to the wound 355, such that the spacing between the microspheres 375 is less than the half-wavelength of the microwaves 260. In one or more embodiments, the microspheres can be introduced or applied to the bottom of the wound 355. The biological solder 370 can be introduced to the wound 355 after the microspheres 375 are introduced to the wound 355. The biological solder 370 can be applied to the wound 355 by using a syringe or other applicator. The uniformity and thickness of the biological solder 370 does not have to be precise because the wavelength of the microwaves 260 is such that the microwaves 260 will penetrate through the biological solder 370 to the two separate biological tissue pieces of the wound 355 regardless of the thickness and/or uniformity of the layer of biological solder 370. In one or more embodiments, the biological solder 370 can include the microspheres 375, and the microspheres 375 will not need to be directly applied to the bottom of the wound 355. In another embodiment, the wound 355 can be treated without the use of the microspheres 375. The barrier layer 360 can be placed about the biological solder 370 after the biological solder 370 is introduced to the wound 355. The barrier layer 360 can prevent the antenna 145 from coming into direct contact with the biological solder 370.

The impedance of the antenna 145 can be matched or substantially matched with the impedance of the wound 355 and surrounding tissue. The impedance of the wound 355 can be affected by the impedance of the biological solder 370 and/or fluids adjacent the wound 355. The impedance of the wound 355 can be determined or calculated using experimental data, publicly available data, or otherwise. The impedance of the antenna 145 can be matched or substantially matched to the impedance of the wound 355 by selecting an antenna 145 having a pre-selected impedance that substantially matches the impedance of the wound 355; adjusting the dielectric material 240 within the waveguide 140 and/or the antenna 145; by changing the cross sectional area of the aperture 215 or the waveguide 140 adjacent the antenna 145; or any combination. The impedance of the antenna 145 can be controlled by the dielectric material through its microwave properties, i.e. dielectric constant, conductivity, etc., and by the use of multiple dielectric materials adjacent to one another. The thickness of these different dielectric materials will help determine the antenna impedance and the size of its aperture.

In one or more embodiments, the impedance of the antenna 145 can be such that the reflected power to the antenna 145 and the output power of the antenna 145 are equal when the antenna 145 is remote from the barrier layer 360 or biological solder 370. Accordingly, the antenna 145 can be configured to emit very little power therefrom until proximate to or in contact with the barrier layer 360, biological solder 370, or both.

The impedance of the antenna 145 can be such that the antenna 145 has to be touching or within a pre-selected distance of the wound 355, biological solder 370, and/or the barrier layer 360 to provide optimum performance of the microwave welding system 300. The microwave welding system 300 can be at optimum performance when the ratio between the output power from the antenna 145 and the power reflected to the antenna 145 is greater than about 5 decibels. The antenna 145 can be configured to provide optimum performance of the microwave welding system 300 when directly contacting the barrier layer 360 or the biological solder 370, and the performance of the microwave welding system 300 can degrade as the antenna 145 is moved from the barrier layer 360 or biological solder 370. For example, the performance of the microwave welding system 300 can degrade when the antenna 145 is more than a few millimeters from the barrier layer 360 or the biological solder 370.

The microwave system 300 can be turned on and the variable power amplifier 120 can be adjusted to provide a pre-selected output power of the antenna 145 after the impedance of the antenna 145 is properly matched with the impedance of the wound 355. The variable power amplifier 120 can be adjusted to provide a pre-selected output power from the antenna 145 by adjusting the variable attenuator 330. The antenna 145 can be placed adjacent to or on the barrier layer 360 after the output power from the antenna 145 is set, before the output power of the antenna 145 is set, or simultaneously with setting the output power of the antenna 145. The microwaves 260 can be transmitted from the microwave generator 110 through the antenna 145 to weld the two separate biological tissue pieces of the wound 355 together after the antenna 145 is proximate to the barrier layer 360.

The antenna 145 can transmit the microwaves 260 to the biological solder 370 and the two or more biological tissue pieces of the wound 355 when placed proximate to or directly on the barrier layer 360 and/or the biological solder 370. To ensure proper operation of the antenna 145, the output power of the antenna 145 can be monitored by the forward power monitor 150 and the power reflected to the antenna 145 can be monitored by the reflected power monitor 160 as the antenna 145 transmits the microwaves 260 to the biological solder 370 and the two separate biological tissue pieces of the wound 355. The measured forward power data acquired by the first sensor 155 of the forward power monitor 150 and the measured reflected power data acquired by the second sensor 165 of the reflected power monitor 160 can be manually interpreted by any operator, communicated to the processor 310, or both. The measured output power data acquired by the first sensor 155 of the forward power monitor 150 and the measured reflected power data acquired by the second sensor 165 of the reflected power monitor 160 can be used to calculate the ratio between the output power and the reflected power. If the ratio of the output power to reflected power is less than a pre-selected value, such as 5 decibels, corrective action can be taken. The corrective action can include increasing the exposure time of the microwave radiation 260 to the biological solder 370 and the two separate biological tissue pieces of the wound 355, increasing the power output from the microwave welding system 300, changing the impedance of the antenna 145, or shutting down the microwave welding system 300.

In one or more embodiments, the processor 310 can be in communication with the forward power monitor 150, the reflected power monitor 160, the variable power amplifier 120, and/or other portions of the microwave welding system 300 and can calculate the ratio of output power to reflected power and initiate corrective action when the ratio is outside a predetermined range. The corrective action can include the processor 310 initiating the shutdown of microwave welding system 300, adjusting the variable attenuator 330 and/or variable power amplifier 120 to adjust the power output of the microwave welding system 300.

After an appropriate time of emitting the microwave radiation 260 into the biological solder 370 and/or the two separate biological tissue pieces of the wound 355, the heated biological solder 370 can join or weld the two or more biological tissue pieces of the wound 355 together. The appropriate time of emitting microwaves 260 into the biological solder 370 and/or the two or more biological tissue pieces of the wound 355 can range from a low of about 5 seconds, about 15 second, or about 20 seconds to a high of about 60 seconds, about 75 seconds, or about 90 seconds, depending upon the particular type of wound 355.

In one or more embodiments, the microwave welding system 300 can sterilize the two separate biological tissue pieces of the wound 355 being welded together. For example, the microwave welding system 300 can be operated within the Ka-band frequency to ablate (kill) bacteria while performing the welding operation. The microwave conductivity differences between bacteria and biological tissue enables the selective heating and ablating of bacteria when the microwave radiation 260 is at a frequency within Ka-band. As such, when the microwave welding system 300 is operated within the Ka-band, the microwave welding system 300 can simultaneously join the two separate biological tissue pieces of the wound 355 together and kill at least a portion of any microorganisms, e.g. bacteria that may be present.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method for joining biological tissue together comprising:
 applying a biological solder on a wound;
 disposing a barrier layer on the biological solder;
 locating an antenna in proximate spatial relationship to the barrier layer;
 matching an impedance of the antenna to an impedance of the wound; and
 transmitting microwaves from a signal generator through the antenna to weld two or more biological tissue pieces of the wound together, wherein a power of the microwaves is adjusted by a control circuit disposed between the antenna and the signal generator.

2. The method of claim 1, wherein the biological solder comprises bovine serum albumin and sterile water.

3. The method of claim 1, wherein the barrier layer comprises a gauze, a polyester film, a plastic sheet, or any combination thereof.

4. The method of claim 1, further comprising monitoring an output power of the antenna and a power reflected back to the antenna.

5. The method of claim 4, wherein the ratio between the output power and the reflected power is maintained above about 5 decibels.

6. The method of claim 5, further comprising switching the antenna to a second antenna if the ratio between the output power and the reflected power is less than about 5 decibels.

7. The method of claim 1, wherein the microwave has a frequency of about 2 Gigahertz to about 40 Gigahertz.

8. The method of claim 1, further comprising disposing a polymer containing metallic or other reflective particles in the wound before disposing the biological solder on the wound.

9. A method for joining biological tissue together comprising:
 applying a biological solder to a wound;
 disposing a barrier layer on the biological solder;
 locating an antenna in proximate spatial relationship to the barrier layer;
 matching an impedance of the antenna with an impedance of the wound;
 transmitting microwaves from a signal generator through the antenna to weld two or more biological tissue pieces of the wound together, wherein a power of the microwaves is adjusted by a control circuit disposed between the antenna and the signal generator;
 measuring an output power from the antenna using a power monitor in communication with the antenna; and
 measuring a power reflected back to the antenna using a reflected power monitor in communication with the antenna.

10. The method of claim 9, further comprising increasing the output power of the antenna if the ratio between the output power and the reflected power is less than about 5 decibels.

11. The method of claim 9, wherein the biological solder comprises from about 90 to about 100 grams of bovine serum albumin and about 100 milliliters of sterile water.

12. The method of claim 9, wherein the microwave has a frequency of from about 2 Gigahertz to about 40 Gigahertz.

13. The method of claim 9, further comprising simultaneously welding the two or more biological tissue pieces of the wound together and killing at least a portion of any bacteria present about the wound.

14. The method of claim 9, further comprising disposing a polymer containing metallic or other reflective particles in the wound before applying the biological solder to the wound.

15. The method of claim 9, wherein the biological solder comprises a polymer containing metallic or other reflective particles.

16. The method of claim 9, further comprising adjusting the impedance of the antenna to maintain the ratio between the output power from the antenna and the reflected power to the antenna to at least 5 decibels.

17. A method for joining biological tissue together comprising:
 applying a biological solder to a wound;
 disposing a barrier layer on the biological solder;
 locating an antenna in proximate spatial relationship to the barrier layer;
 matching an impedance of the antenna with an impedance of the wound;
 transmitting microwaves from a signal generator through the antenna to weld two or more biological tissue pieces of the wound together, wherein a power of the microwaves is adjusted by a control circuit disposed between the antenna and the signal generator;
 measuring an output power from the antenna using a power monitor in communication with the antenna;
 measuring a power reflected back to the antenna using a reflected power monitor in communication with the antenna; and
 adjusting the impedance of the antenna when the ratio between the output power and the reflected power is less than or equal to about 5 decibels.

18. The method of claim 17, wherein the signal generator generates a microwave at a frequency of about 2 Gigahertz to about 40 Gigahertz.

19. The method of claim 17, further comprising a waveguide disposed between the antenna and the control circuit.

20. The method of claim 17, wherein the control circuit comprises a variable attenuator in communication with a preamp and an amplifier.

* * * * *